US005750764A

United States Patent [19]

Marais et al.

[11] Patent Number: 5,750,764
[45] Date of Patent: May 12, 1998

[54] SYNTHESIS AND RESOLUTION OF PROPIONIC ACID DERIVATIVES

[75] Inventors: Stephanus Francois Marais, Garsfontein; Thebeeapelo John Khaile, Erasmuskloof; Owen Lungile Njamela, Kempton Park; Dana Helen Braithwaite, Johannesburg; Deborah Nicole Davidson, Hurlyvale; Christa Maria Jungmann, Edenvale; Christopher John Parkinson, Modderfontein; Neil Stockenstrom Gardiner, Noordwyk; Lucia Hendrina Steenkamp, Boksburg; Etienne Van Eeden Skein, Randburg, all of South Africa

[73] Assignee: AECI Limited, Johannesburg, South Africa

[21] Appl. No.: 744,187

[22] Filed: Nov. 5, 1996

[30] Foreign Application Priority Data

Nov. 17, 1995 [ZA] South Africa ............... 95/9792
Apr. 30, 1996 [ZA] South Africa ............... 96/3420

[51] Int. Cl.⁶ .................................. C07C 69/76
[52] U.S. Cl. .................................. 560/56
[58] Field of Search .................................. 560/56

[56] References Cited

U.S. PATENT DOCUMENTS

| | | |
|---|---|---|
| 3,637,767 | 1/1972 | Alvarez . |
| 3,658,858 | 4/1972 | Harrison . |
| 3,663,584 | 5/1972 | Alvarez . |
| 3,720,708 | 3/1973 | Halpern . |
| 3,758,544 | 9/1973 | Alvarez . |
| 3,873,594 | 3/1975 | Alvarez . |
| 3,994,968 | 11/1976 | Alvarez . |
| 4,188,491 | 2/1980 | Nicholson et al. . |
| 4,304,931 | 12/1981 | Nicholson et al. . |
| 4,515,811 | 5/1985 | Holton . |
| 4,628,123 | 12/1986 | Borsotti . |
| 4,762,793 | 8/1988 | Cesti et al. . |
| 4,857,462 | 8/1989 | Maier et al. . |
| 4,886,750 | 12/1989 | Bertola et al. . |
| 4,922,010 | 5/1990 | Kashima .................. 562/470 |
| 5,037,751 | 8/1991 | Bertola et al. . |
| 5,144,050 | 9/1992 | Chan et al. . |
| 5,198,561 | 3/1993 | Chan et al. . |
| 5,202,473 | 4/1993 | Chan et al. . |
| 5,229,280 | 7/1993 | Bianchi et al. . |
| 5,233,084 | 8/1993 | Chan . |
| 5,273,895 | 12/1993 | Rossi et al. . |

FOREIGN PATENT DOCUMENTS

| | | |
|---|---|---|
| 0 153 474 | of 0000 | European Pat. Off. . |
| 0 227 078 | of 0000 | European Pat. Off. . |
| 0 330 217 | of 0000 | European Pat. Off. . |
| 0 274 146 | 7/1988 | European Pat. Off. . |
| 0 338 645 | 10/1989 | European Pat. Off. . |
| 0 386 848 | 9/1990 | European Pat. Off. . |
| 76 100042 | 9/1976 | Japan . |
| 77 065243 | 5/1977 | Japan . |
| 78 002449 | 1/1978 | Japan . |
| 89 160941 | 6/1989 | Japan . |
| 86/4254 | 6/1986 | South Africa . |
| 86/9583 | 12/1986 | South Africa . |
| 87/0086 | 1/1987 | South Africa . |
| 89/1308 | 2/1989 | South Africa . |
| 94/20634 | 9/1994 | WIPO . |

OTHER PUBLICATIONS

Qu-Ming Gu et al.; "A Facile Enzymatic Resolution Process for the Preparation of (+)—S—2—(6—Methoxy—2—Naphthyl) Proprionic Acid (Naproxen)"; Tetrahedron Letters, 1986, pp. 1763–1766, vol. 27, No. 16; Pergamon Press Ltd., Great Britain.

*Primary Examiner*—Paul J. Killos
*Attorney, Agent, or Firm*—Marshall & Melhorn

[57] ABSTRACT

A process for the production of disubstituted propionic acid derivatives which are intermediates in the synthesis of α-arylpropionic acids such as naproxen, involves the reaction of a naphthalene derivative such as 2-methoxynaphthalene, with an alkylating agent such as an alkyl pyruvate in the presence of a catalyst, and then dehydrating and hydrogenolising, or directly hydrogenolising, or derivatising and then hydrogenolising the product thereof, to produce the desired compound.

15 Claims, No Drawings

SYNTHESIS AND RESOLUTION OF PROPIONIC ACID DERIVATIVES

BACKGROUND OF THE INVENTION

This invention relates to a process for the production of disubstituted propionic acid derivatives, which are intermediates in the synthesis of α-arylpropionic acids such as naproxen.

There are a vast number of processes available for the synthesis of α-arylpropionic acids. A wide variety of key intermediates are utilised in these syntheses, most of which are prepared via a complicated series of process steps.

A commercial process for the production of (S)-naproxen (disclosed in U.S. Pat. No. 3,637,767, U.S. Pat. No. 3,663,584 and U.S. Pat. No. 3,658,858) entails the methylation of β-naphthol, followed by bromination to form 2-bromo-6-methoxynaphthalene. This product is subjected to a Grignard reaction and then reacted with cadmium chloride to form di-(6-methoxy-2-naphthyl)cadmium which upon treatment with ethyl-2-bromopropionate forms (R,S)-ethyl 2-(6-methoxy-2-naphthyl) propionate. Hydrolysis of the ester yields (R,S)-naproxen. The resolution of (R,S)-naproxen to obtain (S)-naproxen is carried out using for example, cinchonidine. (S)-Naproxen is thus selectively esterified and is then further hydrolysed to (S)-naproxen. The unreacted (R)-naproxen is esterified and subsequently racemised. The racemic ester is hydrolysed and the resolution step repeated.

In a second process, (disclosed in JP 76,100,042), (S)-naproxen is prepared via the acylation of 2-methoxynaphthalene followed by epoxidation. The epoxide is converted to an aldehyde intermediate from which (R,S)-naproxen is obtained by oxidation. The resolution of (R,S)-naproxen is performed in a similar way to that described above.

A further process (disclosed in U.S. Pat. No. 5,144,050) proceeds via a disubstituted propionic acid intermediate such as 2-hydroxy-2-(6-methoxy-2-naphthyl)propionic acid, which is prepared via the acylation of 2-methoxynaphthalene followed by an electrolytic oxidation process. This intermediate is then dehydrated to form 2-hydroxy-2-(6-methoxy-2-naphthyl)propionic acid. Hydrogenation using a chiral catalyst yields (S)-naproxen.

The commercial preparation of 2-hydroxy-2-(6-methoxy-2-naphthyl) propionic acid has also been demonstrated utilising a Grignard reaction (disclosed in U.S. Pat. No. 4,188,491, and U.S. Pat. No. 4,304,931). Either an ester or amide of pyruvic acid or a metal salt of pyruvic acid is reacted with the Grignard reagents derived from 2-bromo-6-methoxynaphthalene, followed by hydrolysis of either the ester or the amide. The resultant hydroxypropionic acid derivative is then either dehydrated and hydrogenated or, alternatively, hydrogenolysed to generate naproxen directly. Enantioselective hydrogenation has also been examined.

An additional process (disclosed in JP 77,65,243) describing the synthesis of a disubstituted propionic acid derivative such as 2-hydroxy-2-(4-isobutylphenyl)propionic acid, proceeds via the bromination of isobutylbenzene to form 4-bromo-isobutylbenzene, which is then treated with magnesium turnings and reacted with a lithium salt of pyruvic acid in the presence of tetrahydrofuran and hexamethylphosphorous triamide at low temperatures to yield 2-hydroxy-2-(4-isobutylphenyl)propionic acid.

In Japanese Patent Application No 53002449 a process is described in which an alkylbenzene is reacted with pyruvic acid in the presence of a condensation agent such as aluminium chloride, sulphuric acid or ferric bromide, to yield the corresponding hydroxypropionic acid. This patent application further describes the conversion of this intermediate to arylpropionic acids, such as ibuprofen, via a hydrogenolysis step. The yields achieved in the alkylation reaction were only moderate (<40%). This patent application only describes the applicability of this process to the alkylation of alkylbenzenes such as isobutylbenzene, which is a precursor to ibuprofen.

Additionally, the alkylation of 2-methoxynaphthalene using pyruvic acid derivatives has been described (disclosed in U.S. Pat. No. 4,922,010 and JP 1160941). The acid derivative is hydrolysed prior to isolation as 2-hydroxy-2-(6-methoxy-2-naphthyl) propionic acid, which is subsequently dehydrated under acidic conditions and the resultant acrylic acid is hydrogenated to generate (R,S)-naproxen.

Several processes are known for selectively producing the required isomer of α-arylpropionic acids. A stereoselective lipase catalysed hydrolysis of naproxen esters to produce (S)-naproxen has been developed (Gu et al. Tetrahedron Lett. 27, 1763–1766 (1986); U.S. Pat. No. 4,762,793; EP 0,227,078; EP 0,330,217; SA 89/1308). The enantioselective esterase catalysed hydrolysis of the (S-)naproxen ester to produce (S)-naproxen has also been described (SA 87/0086; EP 0,153,474; U.S. Pat. No. 4,886,750; U.S. Pat. No. 5,037,751). Another process describes the microbial oxidation of 2-(6-methoxy-2-naphthyl)heptane to produce (S)-naproxen (EP 274,146). Stereospecific enzymatic inversion of (R)-naproxen to (S)-naproxen using microorganisms (EP 338,645, EP 386,848) has been documented, as has the microbially directed stereospecific oxidative conversion of an aldehyde to chiral carboxylic acids which may include α-arylpropionic acids (U.S. Pat. No. 5,273,895).

SUMMARY OF THE INVENTION

According to the invention there is provided a process for the production of a compound of formula V

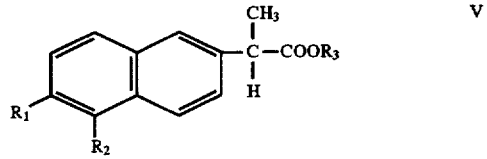

wherein $R_1$ represents a group $OR_6$, wherein $R_6$ represents H or a $C_1$–$C_3$ alkyl group;

$R_2$ represents H or $X_1$, wherein $X_1$ represents I, Br, Cl, F or $SO_3H$; and $R_3$ represents a $C_1$–$C_{18}$ alkyl group;

which comprises the steps of:

(i) reacting a compound of formula I

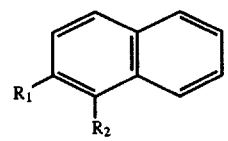

wherein $R_1$ and $R_2$ are as defined above, with an alkylating agent of formula II

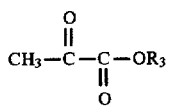

wherein $R_3$ is as defined above,
in the presence of a catalyst to give a compound of formula III

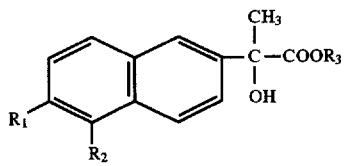

wherein $R_1$ to $R_3$ are as defined above; and either (ii)(a) dehydrating a compound of formula III to give a compound of formula IV

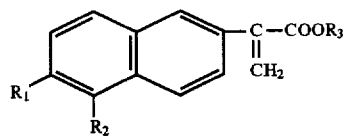

wherein $R_1$ to $R_3$ are as defined above; and (ii)(b) treating a compound of formula IV with hydrogen in the presence of a catalyst to give a compound of the formula V; or (iii) hydrogenolysing a compound of formula III directly to give a compound of formula V; or (iv)(a) derivatising a compound of formula III to give a compound of formula VI

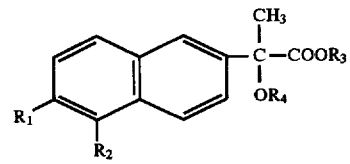

wherein $R_4$ represents $COR_5$ or a $C_1$–$C_5$ alkyl group, and $R_5$ represents H or a $C_1$–$C_6$ alkyl group; and (iv)(b) hydrogenolysing a compound of formula VI to give a compound of formula V; or (iv)(c) eliminating the group —$OR_4$ to give a compound of the formula IV;

and after step (iv)(c)

(iv)(d) treating a compound of formula IV with hydrogen in the presence of a catalyst to give a compound of the formula V.

In step (i) the catalyst may be a Lewis acid catalyst or a Brønstedt acid catalyst or another suitable solid catalyst.

In step (i) the reaction may be carried out in a suitable solvent, although alkylation can be carried out in a melt of the compound of formula I.

In step (ii)(a), in the presence of certain catalysts, dehydration of a compound of formula III to a compound of formula IV may occur in situ. Alternatively, the compound of formula III may first be isolated and then dehydrated to give the compound of formula IV.

Racemic compounds of the formula V may be resolved using a proper microorganism or a substance derived therefrom, generating acids of the formula VII as a single enantiomer.

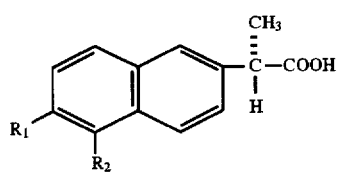

The unreacted enantiomer of formula V can be racemised and the racemate further resolved as required.

DESCRIPTION OF EMBODIMENTS

The crux of the invention is a process for the production of a compound of the formula V, by preparation of a compound of formula III and subsequent hydrogenolysis or dehydration and hydrogenation, which is optionally followed by an enzymic resolution, (incorporating hydrolysis of the ester group at this stage), to a single enantiomer of formula VII.

The various substituents $R_1$ to $R_6$ are as defined above.

When a substituent is an alkyl group, the alkyl group may be straight chain, branched chain or cyclic.

As the process of the invention involves the synthesis of disubstituted alkyl propionates, suitable for further processing to stereochemically pure α-arylpropionic acids such as (S)-naproxen, in the process, the compound of formula I may be 2-methoxynaphthalene or 1-bromo-2-methoxynaphthalene. Further, the compound of the formula II may be an alkyl α-ketoester such as the alkyl esters of pyruvic acid.

Step (i) of the reaction is carried out in the presence of a catalyst which may be a Lewis acid catalyst such as $AlCl_3$, substituted aluminium chlorides (where one or two of the chloride residues have been substituted with an alkyl or alkoxy group eg dichloroaluminium iso-propoxide), $SnCl_4$, boron halides eg $BF_3$ or $BBr_3$, zinc halides eg $ZnCl_2$ or $ZnBr_2$, $FeCl_3$, trimethylsilyl trifluoromethanesulfonate, toluenesulfonic acid, or titanium tetrachloride, or a Brønstedt acid such as HCl, HF, $H_2SO_4$, organic sulfonic acids or $H_3PO_4$; or a suitable supported catalyst such as Envirocat EPIC which is a polyphosphoric acid on a support, or Envirocat EPZ10 which is ferric chloride on a support or a solid phosphoric acid, or a suitable zeolite catalyst. The preferred catalyst is aluminium chloride.

Step (i) of the reaction is preferably carried out in a solvent, although alkylation can be carried out in a melt of the compound of formula I.

The solvent may be any solvent known to be capable of stabilising electrophiles in solution, such as nitrobenzene, nitromethane, acetonitrile or acetone, but may also be a chlorinated solvent such as dichloromethane, chloroform or dichloroethane, or an aromatic solvent, such as xylene, toluene, ethers (both cyclic, eg tetrahydrofuran, and open chain), mono- or dichlorobenzene, acetic acid, cyclohexane, diethyl ether, and simple alcohols eg isopropyl alcohol. Combinations of these solvents may also be used. The preferred solvent is dichloromethane.

The process may be carried out by slow or fast addition of the alkylating agent compound II, to a mixture of the catalyst, solvent and compound I, and also by either slow or fast addition of compound I to a mixture of the solvent, catalyst and alkylating agent compound II. The reaction may also be carried out by simultaneous addition of the alkylating agent (compound II) and compound I to a mixture of the solvent and catalyst, or by addition of the catalyst to a mixture of compounds I and II in the solvent. The preferred process is to add the compound II last.

In the process the reaction temperature during and after addition may be any temperature below the boiling point of the chosen solvent or the reflux temperature of the mixture, or even higher temperatures when the reaction is carried out under pressure. The temperature is preferably in the range from −70° C. to the boiling point of the solvent, more preferably from −20° C. to 10° C. inclusive.

Step (i) of the reaction may be carried out in air or under an inert atmosphere such as argon or nitrogen, at reduced, elevated or atmospheric pressure.

After the completion of the reaction of step (i), the catalyst is removed or deactivated and the solvent is removed. The required alkyl 2-hydroxy-2-arylpropionate is isolated from the reaction mixture by selective extraction, selective crystallisation from a number of solvents or removal of the more volatile components of the mixture by either vacuum or steam distillation. Alternatively, the reaction mixture can be used without purification in the next stage of the process.

The compound of formula III can be either dehydrated to a compound of formula IV, followed by subsequent hydrogenation, or hydrogenolysed directly without dehydration, or the hydroxyl group can be derivatised and the derivative of formula VI can be either hydrogenolysed or the —OR$_4$ group can be eliminated and the resultant compound of formula IV can be hydrogenated.

In step (ii)(a) the dehydration of a compound of formula III to a compound of formula IV can be carried out by using an acid in a solvent with or without a free radical trapping agent. The acid may also be used as the solvent where appropriate. The acid may be a Brønstead acid such as sulphuric acid, arylsulfonic acids, phosphoric acid, polyphosphoric acid, acetic acid, hydrochloric acid, hydrofluoric acid or a supported acid such as Envirocat EPIC or a suitable acidic resin such as a Dowex strong acid exchange resin. Lewis acids such as those used in the first step of the process may also be used. The compound of formula IV can also be prepared by treatment of the compound of formula III with potassium hydrogen sulphate in an appropriate solvent such as toluene or acetic acid.

The dehydration can be carried out in either the presence or the absence of a desiccating agent to remove the water produced, or with or without azeotropic removal of water where the solvent is suitable for such a procedure.

In step (ii)(b) the reduction of a compound of formula IV is achieved through hydrogenation, using hydrogen gas over a suitable catalyst in the appropriate solvent at atmospheric or greater pressure.

The solvent for the procedure can be any solvent typically used for catalytic hydrogenation, such as alcohols eg ethanol, carboxylic acids eg formic acid, ethyl acetate and toluene. The preferred solvent is acetic acid.

The catalyst used for the process can be a catalyst typically used in catalytic hydrogenation such as rhodium, ruthenium, nickel, cobalt, platinum or palladium catalysts, or bimetallic combinations thereof, particularly those adsorbed on to carbon.

In step (iii) a compound of formula V can also be prepared by direct hydrogenolysis of a compound of formula III by either treatment with hydrogen gas at atmospheric or elevated pressure in a suitable solvent over a suitable catalyst, or treatment of a compound of formula III with a suitable hydrogen transfer reagent such as formic acid over a suitable catalyst. The catalyst and solvent used may be as described above.

In step (iv)(a) a compound of formula III may be treated in such a manner that the hydroxyl group is derivatised prior to dehydration and subsequent hydrogenation described above. Lower aliphatic acids such as acetic acid with or without a quantity of the analogous anhydride are particularly appropriate for this purpose. The derivatised compound of formula VI can be isolated and purified, but is more usually submitted to hydrogenolysis conditions in step (iv)(b) directly. Derivatisation can be carried out in situ, over the hydrogenation catalyst and under an atmosphere of hydrogen to generate the required racemic compound of formula V directly.

In step (iv)(c) the group —OR$_4$ in a compound of the formula VI may be eliminated to give a compound of formula IV, whereafter the compound of formula IV may be treated with hydrogen in the presence of a catalyst to give a compound of the formula V, as detailed above. Preferably, this entire sequence is carried out as a single process.

Finally, the compound of formula V can, optionally, be resolved to a compound of formula VII using a proper microorganism or substances derived therefrom. Microorganisms capable of performing this reaction are substances capable of emulating lipase or esterase enzyme activity. The reaction can thus be performed by using the microorganisms and/or their growth medium or by isolating the lipase or esterase enzymes by known methods and using the isolated enzymes, with may be in free or immobilised form.

By the term proper microorganism is meant, for example, microorganisms (bacteria, yeasts, fungi or actinomycetes) which may belong to the genera Pseudomonas, Agrobacterium, Corynebacterium, Aerobacter, Bacillus, Brevibacterium, Achromobacter, Aeromonas, Alcaligenes, Arthrobacter, Entereobacter, Erwinia, Escherichia, Klebsiella, Micrococcus, Proteus, Serratia, Xanthomonas, Streptomyces, Actinomyces, Mycobacterium, Nocardia, Aspergillus, Penicillium, Ophiostoma, Ceratocystis and Candida. Microorganisms which may have gained the ability for stereoselective conversion of compounds of formula V to single enantionmers of the formula VII through the introduction of genetic material are also embodied by the term proper microorganism. Organisms of the type *Ceratoctstis ulmi* are particularly suitable.

The enzyme may also be in a commercially available form, such as the lipases from *Candida antarctica* (Novo) and *Candida rugosa* (cylindracea) (Amano AY). Other sources of the enzyme are commercially available kits, for example Chirazyme (Boehringer), ChiroCLEC-CR (Altus) and Chiroscreen (Altus).

Preferably, the reaction using the lipase occurs at a temperature of between 25° and 70° C., with the preferred range being 40°–60° C. A pH is selected from the range of pH 4–9, with the preferred range being pH 5–6. The pH can be optionally controlled at a specific value or changed to a different pH by addition of a suitable acid or base to the reaction mixture.

The conversion of a compound of formula V to a single enantiomer of formula VII can occur in aqueous medium, preferably a buffered solution, or in the presence of a solvent or a mixture of solvents. For example, a water-miscible solvent, such as ethanol, tert-butyl alcohol, n-butyl alcohol, iso-propyl alcohol, isoamylalcohol, dimethylformamide, dimethylsulfoxide, acetone, tetrahydrofuran, 1,4-dioxane, acetonitrile, polyethylene glycol, ethanediol, formaldehyde or 2,4-dimethylpentane-2,4-diol may be added in the concentration range of 1–10% by volume. Alternatively a water-immiscible solvent, for example chloroform, dichloromethane, toluene, diisopropylether, cyclohexane, heptane or ethylacetate, may be added to a concentration of between 1 and 60% by volume. The substrate:solvent ratio preferably falls within the range of 0.005% and 80% (m/v). The ratio of enzyme:substrate is preferably between 1:2.5 and 1:1000.

The conversion of a compound of formula V to a single enantiomer of formula VII can be performed under agitated conditions. It can also be performed using sonication.

Examples of the invention are given below.

Example 1

Dichloromethane (30 mL) and 2-methoxynaphthalene (5 g, 31.7 mmol) were charged to a 3-necked round bottom flask equipped with a thermometer and stirrer and cooled to between 0°–5° C. Aluminium chloride (7 g, 52.5 mmol) was added to the reaction mixture, maintaining the temperature below 10° C. Ethyl pyruvate (5.38 g, 46.3 mmol) in dichloromethane (20 mL) was added over one hour maintaining the temperature below 10° C. After addition the reaction was heated to reflux and refluxed for 2 hours.

The reaction mixture was added to a water/ice mixture (50 mL) and the layers separated. The organic layer was concentrated to generate crude (R,S)-ethyl 2-hydroxy-2-(6-methoxy-2-naphthyl)propionate. The crude was dissolved in acetone and the insoluble matter removed. After removal of solvent, the remainder was recrystallised from diisopropyl ether to give (R,S)-ethyl 2-hydroxy-2-(6-methoxy-2-naphthyl)propionate (6.6 g, 24.1 mmol, 98% pure).

Example 2

Dichloromethane (20 mL) and 2-methoxynaphthalene (1.28 g, 8.09 mmol) were charged to a 3-necked round bottom flask equipped with a thermometer and stirrer and cooled to between 0°–5° C. Aluminium chloride (1.62 g, 12.2 mmol) was added to the reaction mixture, maintaining the temperature below 10° C. Methyl pyruvate (0.83 g, 8.09 mmol) in dichloromethane (10 mL) was added over one hour maintaining the temperature below 10° C. After addition the reaction was stirred at 5° C. for 6 hours.

The reaction mixture was added to a water/ice mixture (20 mL) and the layers separated. The organic layer was concentrated to generate crude (R,S)-methyl 2-hydroxy-2-(6-methoxy-2-naphthyl)propionate. The crude was dissolved in acetone and the insoluble matter removed. After removal of solvent, the remainder was recrystallised from diisopropyl ether to give (R,S)-methyl 2-hydroxy-2-(6-methoxy-2-naphthyl)propionate (1.26 g, 4.85 mmol, 93% pure).

It is to be noted that the results of this example have been subsequently proven to be overquantified, due to non-separation of isomers, by about 20–25%.

Example 3

Nitrobenzene (20 mL) and 2-methoxynaphthalene (1.28 g, 8.09 mmol) were charged to a 3-necked round bottom flask equipped with a thermometer and stirrer and cooled to between 5°–10° C. Aluminium chloride (1.62 g, 12.2 mmol) was added to the reaction mixture, maintaining the temperature below 10° C. Ethyl pyruvate (1.41 g, 46.3 mmol) in nitrobenzene (10 mL) was added over one hour maintaining the temperature below 10° C. After addition the reaction was heated to 50° C. and maintained at this temperature for 2 hours.

The reaction mixture was added to a water/ice mixture (10 mL) and the organic material was extracted in to dichloromethane (2×40 mL). The dichloromethane was removed and hexane was added to precipitate crude (R,S)-ethyl 2-hydroxy-2-(6-methoxy-2-naphthyl)propionate. The crude was dissolved in acetone and the insoluble matter removed. After removal of solvent the filtrate yielded (R,S)-ethyl 2-hydroxy-2-(6-methoxy-2-naphthyl)propionate (0.53 g, 1.94 mmol, 88% pure).

It is to be noted that the results of this example have been subsequently proven to be overquantified, due to non-separation of isomers, by about 15–20%

Example 4

Dichloromethane (20 mL) and aluminium chloride (1.62 g, 12.2 mmol) were charged to a 3-necked round bottom flask equipped with a thermometer and stirrer and cooled to below 0° C. A solution of 2-methoxynaphthalene (1.28 g, 8.09 mmol) and ethyl pyruvate (0.94 g, 8.09 mmol) in dichloromethane (10 mL) was added over one hour maintaining the temperature below 0° C. After addition the reaction was stirred at 0° C. for 2 hours.

The reaction mixture was added to a water/ice mixture (20 mL) and the layers separated. The organic layer was concentrated to generate crude (R,S)-ethyl 2-hydroxy-2-(6-methoxy-2-naphthyl)propionate. The crude was dissolved in acetone and the insoluble matter removed. After removal of solvent, the remainder was recrystallised from diisopropyl ether to give (R,S)-ethyl 2-hydroxy-2-(6-methoxy-2-naphthyl)propionate (1.02 g 3.72 mmol). The balance of the material was recovered as 2-methoxynaphthalene.

It is to be noted that the results of this example have been subsequently proven to be overquantified, due to non-separation of isomers, by about 15–20%.

Example 5

Potassium hydrogensulfate was fused at high temperature under nitrogen and subsequently ground to a powder to generate anhydrous material (20.83 g). This material was dispersed in toluene (60 mL) and (R,S)-ethyl 2-hydroxy-2-(6-methoxy-2-naphthyl)propionate (5.0 g, 18.2 mmol) and butylated hydroxytoluene (60 mg) were added. The mixture was refluxed for 3 hours, allowed to cool, filtered and the residue was washed with dichloromethane (2×50 mL). The solvent was removed from the filtrate and the resultant was recrystallised from ethyl acetate/hexanes and ethyl 2-(6-methoxy-2-naphthyl)acrylate (2.9 g, 11.3 mmol) was isolated.

It is to be noted that the results of this example have been subsequently proven to be overquantified, due to non-separation of isomers, by about 15–20%.

Example 6

Strong cation exchange resin (Dowex HCR-W2) (0.50 g), (R,S)-ethyl 2-hydroxy- 2-(6-methoxy-2-naphthyl) propionate (0.50 g, 1.82 mmol) and butylated hydroxytoluene (1 mg) were refluxed in dry acetic acid (10 mL) for 30 minutes. The solution was cooled and the acidic resin was removed by filtration.

To the filtrate was added a hydrogenation catalyst (4.8% Pd, 0.2% Pt on carbon, 0.05 g) and the mixture was placed under an atmosphere of hydrogen gas at 1000 kPa and warmed to 120° C. for 4 hours. The mixture was allowed to cool and the catalyst was removed by filtration and the residue was washed with ethanol (2×20 mL). The solvent was removed and the residue was crystallised from ethyl acetate/hexanes to produce (R,S)-ethyl 2-(6-methoxy-2-naphthyl)propionate (0.278 g, 1.07 mmol).

It is to be noted that the results of this example have been subsequently proven to be overquantified, due to non-separation of isomers, by about 15–20%.

Example 7

Palladium/platinum (4.8%/0.2%) on carbon (1.0 g) was dispersed in dry acetic acid (20 mL) and exposed to hydrogen gas at 1000 kPa at room temperature for 1 hour, followed by addition of (R,S)-ethyl 2-hydroxy-2-(6-methoxy-2-naphthyl)propionate (1.0 g, 3.65 mmol). Hydrogen was added to a pressure of 1000 kPa and the reaction vessel was heated to 110° C. for 4 hours. The catalyst was removed by filtration and washed with ethanol (2×20 mL). The solvent was removed and the residue was crystallised from ethyl acetate/hexanes to produce (R,S)-ethyl 2-(6-methoxy-2-naphthyl)propionate (0.292 g, 1.13 mol).

Example 8

Palladium (5%) on carbon (50 mg) was dispersed in dry acetic acid (20 mL) and exposed to hydrogen gas at 1000 kPa at room temperature for 1 hour, followed by addition of (R,S)-ethyl 2-hydroxy-2-(6-methoxy-2-naphthyl)propionate (1.0 g, 3.65 mmol) and acetic anhydride (0.45 g, 4.01 mmol). Hydrogen was added to a pressure of 1000 kPa and the reaction vessel was heated to 120° C. for 18 hours. The catalyst was removed by filtration and washed with ethanol (2×20 mL). The solvent was removed and the residue was crystallised from ethyl acetate/hexanes to produce (R,S)-ethyl 2-(6-methoxy-2-naphthyl)propionate (0.734 g, 2.85 mmol).

Example 9

Palladium (10%) on carbon (200 mg) was dispersed in ethanol (25 mL) and exposed to hydrogen gas at 1000 kPa at room temperature for 1 hour, followed by addition of (R,S)-ethyl 2-hydroxy-2-(6-methoxy-2-naphthyl)propionate (1.0 g, 3.65 mmol). Hydrogen was added to a pressure of 1000 kPa and the reaction vessel was heated to 100° C. for 15 hours. The catalyst was removed by filtration and washed with ethanol (2×20 mL). The solvent was removed and the residue was crystallised from ethyl acetate/hexanes to produce (R,S)-ethyl 2-(6-methoxy-2-naphthyl)propionate (0.423 g, 1.64 mmol).

Example 10

Ethyl 2-(6-methoxy-2-naphthyl)acrylate (2.7 g, 10.5 mmol) from Example 6 was dissolved in ethanol (40 mL) and 5% palladium on carbon (0.27 g) was added. The mixture was stirred under hydrogen at 200 kPa and room temperature for 18 hours. The catalyst was removed by filtration and washed with ethanol (2×20 mL). The solvent was removed and the residue was crystallised from ethyl acetate/hexanes to produce (R,S)-ethyl 2-(6-methoxy-2-naphthyl)propionate (2.19 g, 8.50 mmol).

Example 11

(R,S)-ethyl 2-(6-methoxy-2-naphthyl)propionate (100 mg, 0.39 mmol) and ChiroCLEC-CR lipase (1 mg) were added to PEG-Acetate buffer (50% PEG 1000, 50% 0.5M acetate pH 5, 1 mL). The reaction mixture was incubated at 40° C. for 4 hours in a sonicating water bath. After 4 hours, the reaction was stopped with acetonitrile (1 mL). Sample analysis was performed according to Example 1 above. A productivity six times higher than that obtained with stirring was observed. The ee obtained was 99.5% for (S)-naproxen.

Example 12

Dichloromethane (30 mL) and 2-methoxynaphthalene (5 g, 31.7 mmol) were charged to a 3-necked round bottom flask equipped with a thermometer and stirrer and cooled to between 0°–5° C. Aluminium chloride (7 g, 52.5 mmol) was added to the reaction mixture, maintaining the temperature below 10° C. Ethyl pyruvate (5.38 g, 46.3 mmol) in dichloromethane (20 mL) was added over one hour maintaining the temperature below 10° C. After addition the reaction was heated to reflux and refluxed for 0.75 hours and poured on to ice. The organic phase showed formation of ethyl 2-hydroxy-2-(6-methoxynaphth-2-yl)propionate with a selectivity of 98% at a conversion of 82%.

The crude material so generated was dissolved in acetone, cooled, and the insoluble matter removed by filtration. After removal of solvent, the remainder was recrystallised from diisopropyl ether to give (R,S)-ethyl 2-hydroxy-2-(6-methoxy-2-naphthyl)propionate (98% pure).

Example 13

Dichloromethane (20 mL) and 2-methoxynaphthalene (2.73 g, 17.3 mmol) were charged to a 3-necked round bottom flask equipped with a thermometer and stirrer and cooled to between 0°–5° C. Aluminium chloride (3.45 g, 25.9 mmol) was added to the reaction mixture in three equal portions, maintaining the temperature below 7° C. Isopropyl pyruvate (3.37 g, 25.9 mmol) in dichloromethane (7.3 mL) was added over 35 minutes maintaining the temperature below 7° C. After addition the reaction was stirred at a temperature of 4°–7° C. for 1 hour.

The reaction mixture was added to a water/ice mixture (50 mL) and the layers separated. The organic layer was concentrated to generate crude (R,S)-isopropyl 2-hydroxy-2-(6-methoxy-2-naphthyl)propionate. The crude was dissolved in acetone and the insoluble matter removed. After removal of solvent, the remainder was recrystallised from diisopropyl ether to give (R,S)-isopropyl 2-hydroxy-2-(6-methoxy-2-naphthyl)propionate (34% yield at 86% purity.)

Example 14

Aluminium chloride (1.62 g, 12.2 mmol) was added in 3 portions to a solution of 2-methoxynaphthalene (1.28 g, 8.09 mmol) in tetrahydrohydrofuran (20 mL) at 5° C. Ethyl pyruvate (1.41 g, 12.2 mmol) in tetrahydrofuran (10 mL) was added oveer 1 hour at this temperature. The reaction was allowed to proceed for 1 hour and warmed to 20° C. for 1 hour. Ethyl 2-hydroxy-2-(6-methoxynaphth-6-yl)propionate was formed in 2% yield with 98% recovery of the starting material.

Example 15

A mixture of 2-methoxynaphthalene (20.0 g, 126 mmol) and methyl pyruvate (19.3 g, 190 mmol) in dichloromethane (100 mL) was added to a suspension of aluminium chloride (25.3 g, 190 mmol) in dichloromethane (100 mL) at 6° C. over 140 minutes. The solution was stirred for a further 15 minutes at this temperature and added to ice/water. Methyl 2-hydroxy-2-(6-methoxynaphth-2-yl)propionate (52% yield) and 2-methoxynaphthalene (34% recovery) were the primary components of the reaction mixture.

Example 16

Aluminium chloride (2.49 g, 18.7 mmol) was added in 2 portions to a solution of 2-methoxynaphthalene (1.97 g, 12.5 mmol) in dichloromethane (15 mL) at 5° C. The red solution was cooled to −20° C. and the reaction vessel was evacuated to a pressure of 160 mbar. Ethyl pyruvate (2.17 g, 18.7 mmol) in dichloromethane (pre-cooled, 5 mL) was added over 5 minutes and the temperature was further reduced to −40° C. The reaction was allowed to proceed for 2 hours, at which time the system was opened to the atmosphere and poured on to ice. Ethyl 2-hydroxy-2-(6-methoxynaphth-6-yl)propionate was formed with a selectivity of 35% at 62% conversion of the starting material.

This material could be prepared for the hydrogenation sequence by removal of volatile components at 100 mbar and removal of 2-methoxynaphthalene at 10 mbar (135°–150° C.). The distillation residue was successfully used in the following step without further purification.

Example 17

Ethyl pyruvate (1.64 g, 14.1 mmol) in dichloromethane (5 mL), was added to a mixture of 1-bromo-2-methoxynaphthalene (2.23 g, 9.41 mmol) and aluminium chloride (1.88 g, 14.1 mmol) in dichloromethane (20 mL) at 5° C. over 30 minutes. The mixture was stirred at 5° C. for a further 1.5 hours and poured on to ice. Ethyl 2-hydroxy-2-(5-bromo-6-methoxynaphth-2-yl)propionate was formed in 11% yield. $^1$HNMR δ (CDCl$_3$) 1.24 (3H,t), 1.85 (3H,s), 4.00 (3H,s), 4.26 (2H,q), 7.2–8.2 (5H$_2$m).

Example 18

2-Methoxynaphthalene (2.11 g, 13.4 mmol) and ethyl pyruvate (2.32 g, 20.0 mmol) in 1,2-dichloroethane (8 mL) were added to a suspension of aluminium chloride (2.67 g, 20.0 mmol) in 1,2-dichloroethane (14 mL) at 5° C. over a period of 30 minutes. The reaction was stirred at his temperature for a further 30 minutes and poured on to ice. The phases were allowed to separate and the organic phase was collected. The solvent was removed leaving an oil (4.16 g) comprising starting material (0.92 g, corresponding to a conversion of 56%), ethyl 2-hydroxy-2-(6-methoxynaphth-2-yl)propionate (0.23 g) and ethyl 2,2-bis(6-methoxynaphth-2-yl)propionate (0.23 g).

Example 19

A solution of 2-methoxynaphthalene (2.58 g, 16.3 mmol) and ethyl pyruvate (2.84 g, 24.5 mmol) in dichloromethane (10 mL) was added to a solution of BBr$_3$ (1.0M in CH$_2$Cl$_2$, 24.5 ml) at 5° C. over 70 minutes. The solution was stirred at 5° C. for 1 hour, warmed to 20° C. and stirred for 1 further hour. the solution was poured in to ice/water. The organic phase was found to contain ethyl 2-hydroxy-2-(6-methoxynaphth-2-yl)propionate (0.057 g,1.3%) and ethyl 2-(6-methoxynaphth-2-yl)acrylate (0.227 g, 5.4%).

Example 20

Iso-propyl alcohol (0.50 g, 31.1 mmol) was added to a suspension of aluminium chloride (4.15 g, 31.1 mmol) in dichloromethane (20 mL) at −5° C. The solution became homogeneous and stirring was continued for 1 minutes. A solution of 2-methoxynaphthalene (3.28 g, 20.8 mmol) and ethyl pyruvate (3.61 g, 31.1 mmol) in dichloromethane (15 mL) was added to this solution at −5° C. over 30 minutes. The solution was allowed to stir at this temperature for a further 30 minutes, warmed to 0° C. and stirred for a further 30 minutes. The solution was poured on to ice to decompose the catalyst. The organic phase contained ethyl 2-hydroxy-2-(6-methoxynaphth-2-yl)propionate (0.83 g, 15%) and unreacted 2-methoxynaphthalene (2.62 g, 80%).

Example 21

Aluminium chloride (162 g, 12.2 mmol) was added in 3 portions to a solution of 2-methoxynaphthalene (1.28 g, 8.09 mmol) in nitromethane (20 mL) at 5° C. Ethyl pyruvate (1.41 g, 12.2 mmol) in nitromethane (10 mL) was added over 1 hour at this temperature. The reaction was allowed to proceed for 1 hour and warmed to 20° C. for 2 hours. Ethyl 2-hydroxy-2-(6-methoxynaphth-6-yl)propionate was formed with a selectivity of 16% at 52% conversion of the starting material.

Example 22

Ethyl 2-hydroxy-2-(6-methoxynaphth-2-yl)propionate (5.0 g, 18.2 mmol), Dowex HCR-W2 strong acid exchange resin (0.50 g) and acetic anhydride (4.09 g, 40.1 mmol) were added to acetic acid (100 g) and refluxed for 7 hours, cooled and the resin was removed by filtration. Ethyl 2-(6-methoxynaphth-2-yl)acrylate was produced in 64.6% yield and could be used without purification.

Palladium catalyst (0.024 g, Johnson-Matthey 338) was added to the solution of the acrylate and the solution was warmed to 100° C. under a 5 bar hydrogen pressure. The reaction mixture was maintained at 5 bar and 100° C. for 14.5 hours, cooled and the solvent was removed after filtration of the catalyst. The residue was washed with saturated sodium hydrogen carbonate solution and extracted in to dichloromethane. The organic phase was dried (MgSO$_4$) and the solvent was removed. The entire sequence resulted in a 28% selectivity to ethyl 2-(6-methoxynaphth-2-yl)propionate at quantitative conversion of the starting material.

Example 23

Ethyl 2-hydroxy-2-(6-methoxynaphth-2-yl)propionate (0.25 g, 0.91 mmol) and butylated hydroxytoluene (0.029 g) were added to toluene (5.75 mL) and the solution was refluxed for 4 hours with azeotropic removal of water. The solvent was removed from 22% of ethyl 2-(6-methoxynaphth-6-yl)acrylate was formed with the balance of the reaction mixture remaining unchanged as the starting material.

Example 24

A mixture of freshly fused KHSO$_4$(2.50 g, 18 mmol), ethyl 2-hydroxy-2-(6-methoxynaphth-2-yl)propionate (0.60 g, 2.19 mmol), butylated hydroxytoluene (0.007 g) and toluene was refluxed for 22 hours. The mixture was filtered hot and the residue was washed with hot dichloromethane (3×30 ml). The solvent was removed and the crude oil was submitted to flash chromatography on silica gel, giving ethyl 2-(6-methoxynaphth-2-yl)acrylate (0.088 g, 16%) as a white solid.

This material in ethanol (5 g) was added to a suspension of a bimetallic platinum/palladium catalyst (5% total on carbon base, 0.05 g) in ethanol (20 g) which had been activated under hydrogen (1000 kPa) for 40 minutes. The reactor was charged with hydrogen (1100 kPa) and the mixture was stirred at 20° C. for 90 minutes. The hydrogen was removed and the catalyst was removed by filtration. The solvent was removed from the filtrate giving ethyl 2-(6-methoxynaphth-2-yl)propionate as the only quantifiable product.

Example 25

Ethyl 2-hydroxy-2-(6-methoxynaphth-2-yl)propionate (7.5 g, 27.3 mmol), acetic anhydride (6.14 g, 60.2 mmol), toluene (37 ml) and palladium catalyst (5% on carbon, 0.75 g) were heated (140° C.) under a hydrogen atmosphere (10 bar) for 14 hours. Ethyl 2-(6-methoxynaphth-2-yl) propionate was formed with a selectivity of 92% at a 2-methoxynaphthalene conversion of 60%.

Example 26

Ethanol (48 g) and palladium catalyst (5% palladium on carbon, 0.12 g) were stirred under a hydrogen atmosphere (10 bar) for 1 hour. The hydrogen was released and ethyl 2-hydroxy-2-(6-methoxynaphth-6-yl)propionate (12.0 g, 43.8 mmol) was added. Hydrogen was charged to the reactor and the vessel was warmed to 160° C. (hydrogen pressure 20 bar). The reactor was stirred at 160° C. for 6 hours and the hydrogen was released. Ethyl 2-(6-methoxynaphth-2-yl) propionate was formed with a selectivity of 35% at 40% conversion of the starting material.

Example 27

Ethyl pyruvate (20.6 g, 177 mmol) and 2-methoxynaphthalene (23.4 g, 148 mmol) in dichloromethane (115 mL) were added to a suspension of aluminium chloride (29.6 g, 222 mmol) in dichloromethane (120 mL) while maintaining the temperature at 0°–5° C. Under these constraints, addition required 1.5 hours. After addition was completed, the reaction mixture was stirred at 4.5° C. for a further 30 minutes. The catalyst was deactivated by pouring the reaction mixture in to ice/water (250 g). The phases were allowed to separate and the organic phase was collected. The solvent was removed and the residue was heated to 95° C. at 80 mbar to remove volatile components.

The residue was added to a solution of acetic acid (56.0 g), acetic anhydride (30.3 g) and palladium catalyst (5% on carbon, 0.37 g) which had been stirred under hydrogen (15 bar) for 2 hours. The reactor was sealed and hydrogen was added. The reactor was warmed to 160° C. (15 bar pressure) and maintained at temperature for 16 hours, cooled and the catalyst was removed by filtration. This resulted in the formation of ethyl 2-(6-methoxynaphth-2-yl)propionate (12, 18 g).

The oily residue was distilled at reduced pressure, collecting the fraction distilling at around 200° C./10 mbar. Ethyl 2-(6-methoxynaphth-2-yl)propionate was recovered (overall yield from 2-methoxynaphthalene 36%, purity 85%). The distillate was recrystallised from ethanol to the required purity.

Example 28

Palladium catalyst (5% Pd on carbon, 0.15 g) and acetic anhydride (12.3 g, 121 mmol) were added to acetic acid (22.7 g) and stirred under an atmosphere of hydrogen (10 bar) for 1 hour. The hydrogen was released and ethyl 2-hydroxy-2-(6-methoxynaphth-2-yl)propionae (15.0 g, 55 mmol) and strongly acidic resin (HRC-W2, 0.15 g) were added to the solvent. The reactor was sealed, charged with hydrogen and warmed to 160° C. over 1 hour (hydrogen pressure 15 bar). The reaction mixture was maintained at 160° C. for a further 5 hours before cooling and removal of the catalyst by filtration. The reaction mixture contained 65% ethyl 2-(6-methoxynaphth-2-yl)propionate and 16% ethyl2-acetoxy-2-(6-methoxynaphth-2-yl)propionate.

Example 29

Palladium catalyst (5% Pd on carbon, 0.025 g) and acetic anhydride (2.05 g, 20 mmol) were added to acetic acid (47.5 g) and stirred under an atomsphere of hydrogen (10 bar) for 1 hour. The hydrogen was released and ethyl 2-hydroxy-2-(6-methoxynaphth-2-yl)propionate (2.5 g, 9.1 mmol) was added to the solvent. The reactor was sealed, charged with hydrogen and warmed to 160° C. over 1 hour (hydrogen pressure 20 bar). The reaction mixture was maintained at 160° C. for a further 5 hours before cooling and removal of the catalyst by filtration. The reaction mixture contained 77% ethyl 2-(6-methoxynaphth-2-yl)propionate, 3% ethyl2-hydroxy-2-(6-methoxynaphth-2-yl)propionate and 2.5% ethyl 2-acetoxy-2-(6-methoxynaphth-2-yl)propionate.

Example 30

Acetic acid (45 g), acetic anhydride (49 g, 480 mmol) and palladium catalyst (5% palladium on carbon 600 mg) were stirred under hydrogen (10 bar) for 2 hours. The hydrogen was removed and a sample containing ethyl 2-hydroxy-2-(6-methoxynaphth-2-yl)propionate (53.1 g) in acetic acid (45 g) was added. The reactor was sealed and warmed to 160° C. under a hydrogen atmosphere (15 bar) and allowed to remain at this temperature for 16 hours. The reactor was cooled and the hydrogen released. The catalyst was removed by filtration and the solvents were removed in vacuo. Ethyl 2-(6-methoxynaphth-2-yl)propionate was the predominant component (48.4 g, 97% yield).

Example 31

Acetic acid (38.8 g), acetic anhydride (6.14 g, 60.2 mmol), ethyl 2-hydroxy-2-(6-methoxynaphth-2-yl) propionate (7.5 g, 27.3 mmol) and palladium catalyst (5% palladium on carbon, 0.375 mg) were stirred under hydrogen (2 bar) for 36 hours at 50° C. The reactor was cooled and the hydrogen released. The catalyst was removed by filtration and the solvents were removed in vacuo. Ethyl 2-(6-methoxynaphth-2-yl)propionate (37%) and ethyl 2-hydroxy-2-(6-methoxynaphth-2-yl)propionate (61%) were the major components of the reaction mixture.

Example 32

(R,S)-ethyl 2-(6-methoxy-2-naphthyl)propionate (R,S-NEE) (2.50 mg, 1.0 mmol) and ChiroCLEC-CR lipase (2 mg) were added to PEG/ammonium acetate buffer (50% PEG 1000; 50% 0.5M ammonium acetate pH 5.1 ml). The reaction mixture was stirred at 600 rmp at a temperature of 55° C. for 5 hours. Following this, the reaction was stopped by the addition of acetonitrile (3 mL). The sample was filtered through cotton wool and analysed by HPLC (% m/m analysis was performed on a reverse phase C-18 column and the R:S ratio determined on a S,S-Whelk column). An E (enantiomeric ratio) of >100 was obtained, with ee (enantiomeric excess) of 99% for S-naproxen.

Example 33

R,S-NEE (250 mg, 1 mmol) was weighed off in a 25 ml round bottom flask and 6.4 ml of cyclohexane added. This was stirred until the ester was dissolved and then 0.6 ml of water was added, whereafter *Candida cylindracea* (rugosa) lipase, obtained from Sigma (0.16 g), was added. The reaction mixture was stirred at 30° C. for 100 hours. Sample analysis was performed according to Example 32. An ee of 93% for S-naproxen was obtained.

Example 34

R,S-naproxen methyl ester (250 mg) was weighed off ina 25 ml round bottom flask and 6.4 ml of chloroform added. This was stirred until the ester was dissolved and then 0.6 ml of water was added, whereafter Lipolase 100T (0.16 g), was added. The reaction mixture was stirred at 30° C. for 100 hours. Sample analysis was performed according to Example 32. A product consisting of >98% S-naproxen was obtained.

Example 35

R,S-NEE (300 mg, 1.16 mmol) and ChiroCLEC-CR lipase (6 mg) were added to PEG/citrate-phosphate buffer (50% PEG 1000; 50% 0.2M citrate-phosphate pH 7, 6 mL). The reaction mixture was stirred at 600 rpm at a temperature of 55° C. for 5 hours. After 5 hours, the reaction was stopped with acetonitrile (3 mL). Sample analysis was performed according to Example 32. An E of >100 was obtained, with ee of 99.4% for S-naproxen.

Example 36

R,S-NEE (250 mg, 1 mmol) and ChiroCLEC-CR lipase (5 mg) were added to PEG/ammonium acetate buffer (50% PEG 1000; 50% 0.2M ammonium acetate pH 5, 1 mL) as well as 2% v/v (solvent/buffer) DMSO (dimethylsulfoxide). The reaction mixture was stirred at 600 rpm at a temperature of 50° C. for 5 hours. After 5 hours, the reaction was stopped with acetonitrile (3 mL). Sample analysis was performed according to Example 32. An E of >100 was obtained, with ee of 98% for S-naproxen.

Example 37

R,S-NEE (2 g) and ChiroCLEC-CR lipase (2 mg; E:S= 1:1000) were added to PEG/ammonium acetate buffer (50% PEG 400; 50% 0.5M ammonium acetate pH 5, 20 mL) The reaction mixture was stirred at a temperature of 55° C. for 22 hours. After 22 hours, the reaction was stopped with acetonitrile (30 mL). Sample analysis was performed according to Example 32. S-Naproxen with an ee of 99.6% was obtained.

Example 38

R,S-NEE (500 mg, 1.94 mmol; 50% m/v) and ChiroCLEC-CR lipase (2 mg) were added to PEG/ammonium acetate buffer (50% PEG 1000; 50% 0.2M ammonium acetate pH 5, 1 mL). The reaction mixture was stirred at 600 rpm at a temperature of 55° C. for 5 hours. After 5 hours, the reaction was stopped with acetonitrile (3 mL). Sample analysis was performed according to Example 32. An E of >100 was obtained, with ee of 99.8% for S-naproxen.

Example 39

R,S-NEE (100 mg, 0.39 mmol) and ChiroCLEC-CR lipase (2 mg) were added to PEG/ammonium acetate buffer (50% PEG 1000; 50% 0.5M ammonium acetate pH 5, 1 mL). The reaction mixture was sonicated for 2 hours with a sonication probe at power output of 2.75 for 5 or 10 seconds on and 30 seconds off. After 2 hours, the reaction was stopped with acetonitrile (1 mL). Sample analysis was performed according to Example 32. A productivity 6 times higher than that obtained with stirring was observed. The product obtained was more than 99.5% S-naproxen.

We claim:
1. A process for the production of a compound of formula V

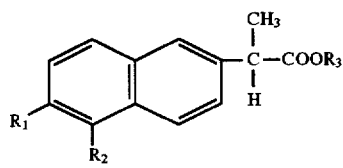

wherein
$R_1$ represents a group $OR_6$, wherein $R_6$ represents H or a $C_1$–$C_3$ alkyl group;
$R_2$ represents H or $X_1$, wherein $X_1$ represents I, Br, Cl, F or $SO_3H$; and
$R_3$ represents a $C_1$–$C_{18}$, alkyl group;
which comprises the steps of:
(i) reacting a compound of formula I

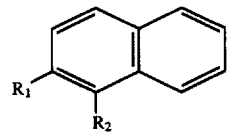

wherein $R_1$ and $R_2$ are as defined above, with an alkylating agent of formula II

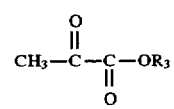

wherein $R_3$ is as defined above,
in the presence of a catalyst to give a compound of formula III

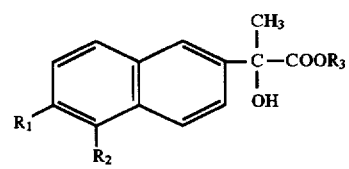

wherein $R_1$ to $R_3$ are as defined above; and either
(ii)(a) dehydrating a compound of formula III to give a compound of formula IV

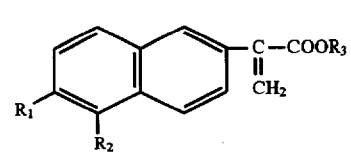

wherein $R_1$ to $R_3$ are as defined above; and
(ii)(b) treating a compound of formula IV with hydrogen in the presence of a catalyst to give a compound of the formula V; or
(iii) hydrogenolysing a compound of formula III directly to give a compound of formula V; or
(iv)(a) derivatising a compound of formula III to give a compound of formula VI

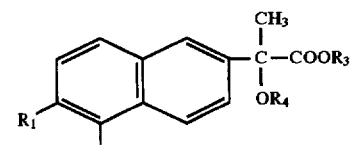

wherein $R_4$ represents $COR_5$ or a $C_1$–$C_5$ alkyl group, and $R_5$ represents H or a $C_1$–$C_6$ alkyl group; and (iv)(b) hydrogenolysing a compound of formula VI to give a compound of formula V; or (iv)(c) eliminating the group —OR$_4$ to give a compound of the formula IV;

and after step (iv)(c)

(iv)(d) treating a compound of formula IV with hydrogen in the presence of a catalyst to give a compound of the formula V.

2. A process according to claim 1 wherein in step (i) the catalyst is selected from the group consisting of a Lewis acid catalyst, a Brønstedt acid catalyst, and a suitable solid catalyst.

3. A process according to claim 1 wherein step (i) is carried out in a solvent.

4. A process according to claim 1 wherein step (i) is carried out in a melt of the compound of formula I.

5. A process according to claim 1 wherein in step (i) the compound of formula I is 2-methoxynaphthalene and the compound of formula II is selected from the group consisting of methyl pyruvate, ethyl pyruvate and isopropyl pyruvate.

6. A process according to claim 1 wherein in step (ii)(a) the dehydration is carried out using an acid optionally in a solvent.

7. A process according to claim 6 wherein the acid is selected from the group consisting of a Brønstedt acid, a supported acid, an acidic resin, and a Lewis acid.

8. A process according to claim 1 wherein in step (ii)(b) the catalyst is selected from the group consisting of rhodium, ruthenium, nickel, cobalt, platinum and palladium catalysts and bimetallic combinations thereof.

9. A process according to claim 1 wherein in step (iii) the hydrogenolysis of a compound of formula III directly to give a compound of formula V is carried out by treatment with hydrogen gas at atmospheric or elevated pressure in a suitable solvent over a suitable catalyst.

10. A process according to claim 1 wherein in step (iii) the hydrogenolysis of a compound of formula III directly to give a compound of formula V is carried out with a suitable hydrogen transfer reagent over a suitable catalyst.

11. A process according to claim 1 wherein in step (iv)(a) the derivatisation of a compound of formula III to give a compound of formula VI is carried out using a lower aliphatic acid.

12. A process according to claim 11 wherein the compound of formula VI from step (iv)(a) is submitted to hydrogenolysis conditions in step (iv)(b) directly.

13. A process according to claim 1 wherein a compound of formula V is resolved into a compound of formula VII using a proper microorganism or a substance derived therefrom.

14. A process for the production of a compound of formula V wherein

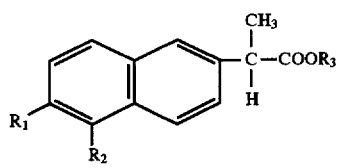

$R_1$ represents a group $OR_6$, wherein $R_6$ represents H or a $C_1$–$C_3$ alkyl group;

$R_2$ represents H or $X_1$, wherein $X_1$ represents I, Br, Cl, F or SO$_3$H; and $R_3$ represents a $C_1$–$C_{18}$ alkyl group;

which comprises the steps of:

(i) reacting a compound of formula I

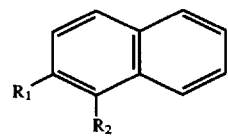

wherein $R_1$ and $R_2$ are as defined above, with an alkylating agent of formula II

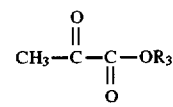

wherein $R_3$ is as defined above, in the presence of a catalyst to give a compound of formula III

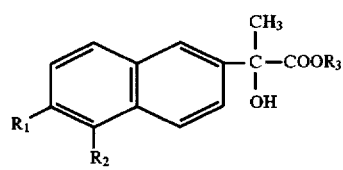

wherein $R_1$ to $R_3$ are defined above; and (ii)(a) dehydrating a compound of formula III to give a compound of formula IV

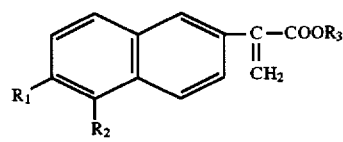

wherein $R_1$ to $R_3$ are as defined above; and (ii)(b) treating a compound of formula IV with hydrogen in the presence of a catalyst to give a compound of the formula V.

15. A process for the production of a compound of formula V

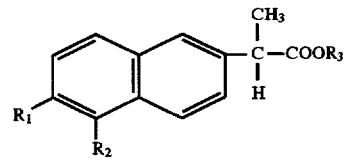

wherein $R_1$ represents a group $OR_6$ represents H or a $C_1$–$C_3$ alkyl group;

$R_2$ represents H or $X_1$, wherein $X_1$ represents I, Br, Cl, or SO$_3$H; and $R_3$ represents a $C_1$–$C_{18}$ alkyl group; which comprises the steps of:

(i) reacting a compound of formula I

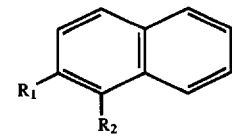

wherein $R_1$ and $R_2$ are as defined above.

with an alkylating agent of formula II

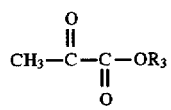   II wherein $R_3$ is defined above,
in the presence of a catalyst to give a compound of formula III

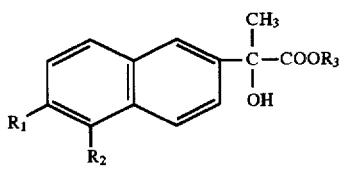   III wherein $R_1$ to $R_3$ are as defined above;

(ii)(a) hydrogenolysing a compound of formulate III directly to give a compound of formula V; or (ii)(b) derivating a compound of formula III to give a compound of formula VI

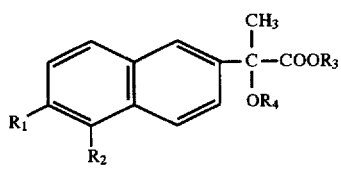   VI wherein $R_4$ represents $COR_5$ or a $C_1$–$C_5$ alkyl group, and $R_5$ represents H or a $C_1$–$C_6$ alkyl group; and (iii)(a) hydrogenolysing a compound of formula VI to give a compound of formula V; or (iii)(b) eliminating the group —$OR_4$ to give a compound of the formula IV; and after step (iii)(b)

(iii)(c) treating a compound of formula IV with hydrogen in the presence of a catalyst to give a compound of the formula V.

* * * * *